(12) United States Patent
Grant et al.

(10) Patent No.: US 8,182,484 B2
(45) Date of Patent: May 22, 2012

(54) ORTHOPAEDIC TRAUMA HIP SCREW ASSEMBLY

(75) Inventors: Stuart R. Grant, Warsaw, IN (US);
Jason Yambor, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 1066 days.

(21) Appl. No.: 12/148,617

(22) Filed: Apr. 21, 2008

(65) Prior Publication Data

US 2009/0264885 A1    Oct. 22, 2009

(51) Int. Cl.
*A61B 17/56* (2006.01)

(52) U.S. Cl. ............................................ 606/66; 606/62

(58) Field of Classification Search ............... 606/62–68
See application file for complete search history.

(56) References Cited

U.S. PATENT DOCUMENTS

| | | | |
|---|---|---|---|
| 4,438,762 A | 3/1984 | Kyle | |
| 4,612,920 A | 9/1986 | Lower | |
| 4,616,638 A | 10/1986 | Griggs | |
| 4,621,629 A | 11/1986 | Koeneman | |
| 4,657,001 A | 4/1987 | Fixel | |
| 4,733,654 A | 3/1988 | Marino | |
| 5,007,910 A | 4/1991 | Anapliotis et al. | |
| 5,032,125 A | 7/1991 | Durham et al. | |
| 5,041,116 A | 8/1991 | Wilson | |
| 5,324,292 A | 6/1994 | Meyers | |
| 5,514,138 A * | 5/1996 | McCarthy | 606/65 |
| 5,693,055 A | 12/1997 | Zahiri et al. | |
| 6,158,437 A * | 12/2000 | Vagley | 128/898 |
| 2004/0193162 A1 | 9/2004 | Bramlet et al. | |
| 2005/0234457 A1* | 10/2005 | James et al. | 606/69 |
| 2006/0106386 A1* | 5/2006 | Reber et al. | 606/65 |

FOREIGN PATENT DOCUMENTS

WO    WO 2006/087159    8/2006

* cited by examiner

*Primary Examiner* — Eduardo C Robert
*Assistant Examiner* — James Palmer
(74) *Attorney, Agent, or Firm* — Maginot, Moore & Beck

(57) ABSTRACT

A fracture reduction assembly and method for insertion of the assembly through a surgical site in one embodiment includes a base portion including a bone contacting surface and an upper surface, a barrel with a first end portion connected to the bone contacting surface, the base portion and the barrel defining a bore extending through the barrel and the base portion and opening at the upper surface of the base portion, a screw portion including a shaft with a first diameter sized to fit within the bore and a threaded portion with a second diameter sized to not fit within the bore, wherein at least a portion of the shaft is positioned within the bore, and a retainer coupled with the shaft and having a third diameter sized to fit within a first portion of the bore but not within a second portion of the bore.

6 Claims, 10 Drawing Sheets

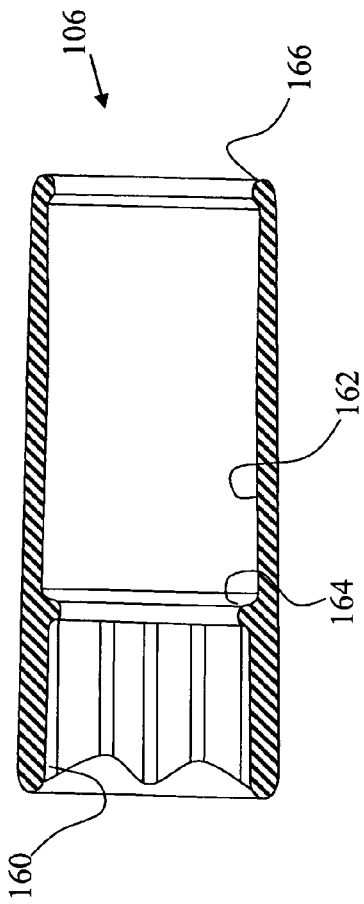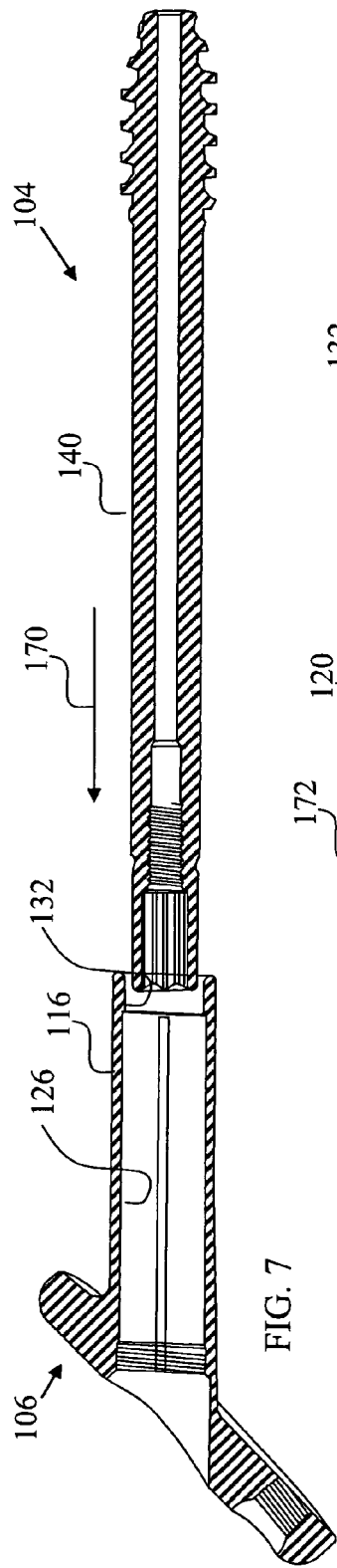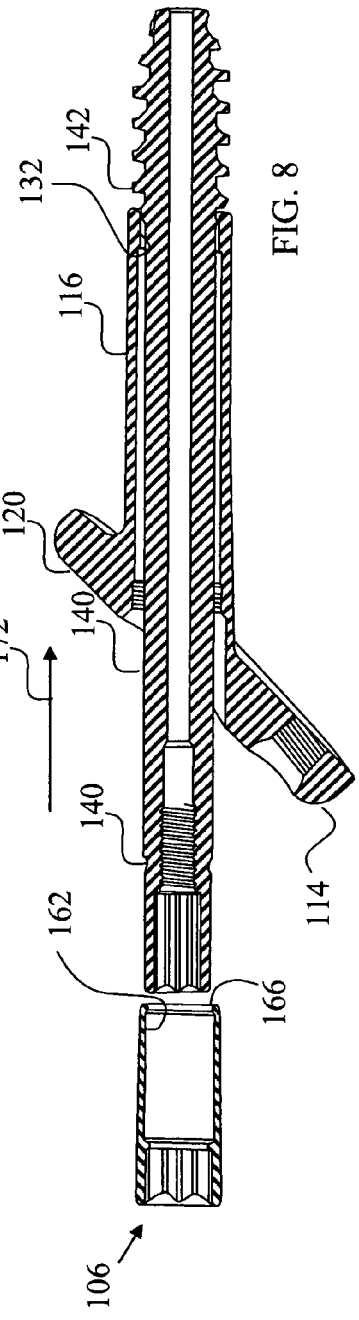

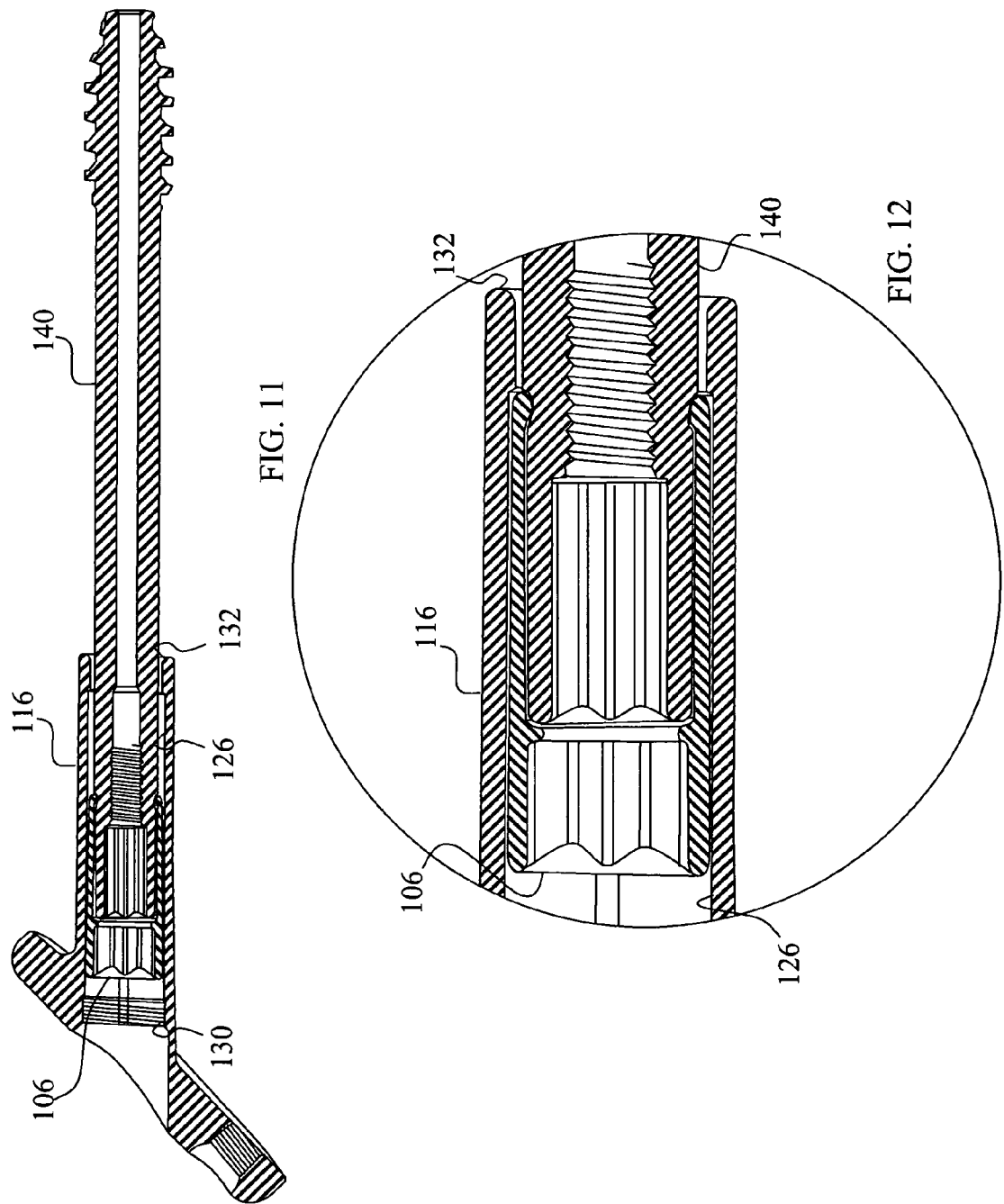

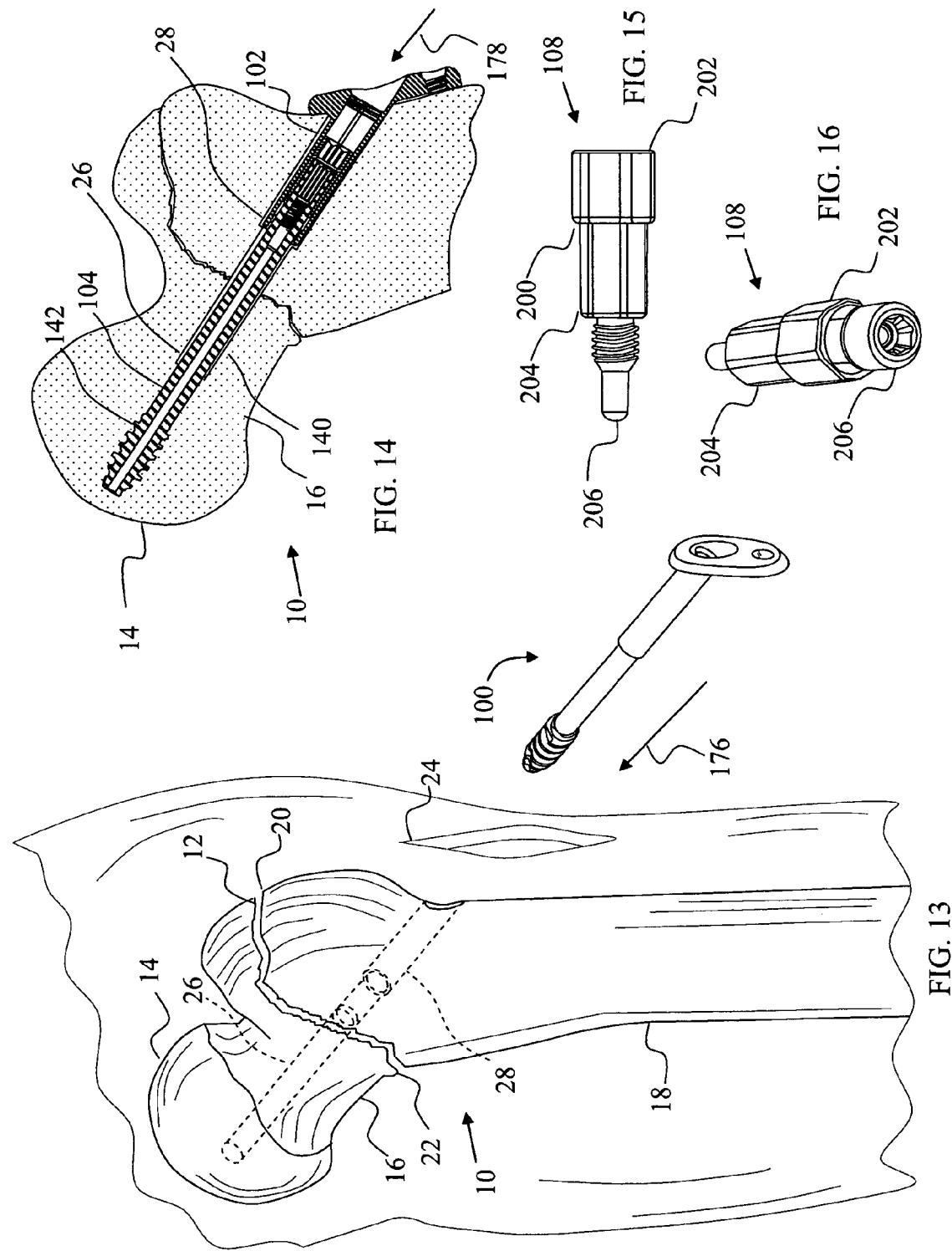

ORTHOPAEDIC TRAUMA HIP SCREW ASSEMBLY

FIELD

This application relates generally to the field of orthopaedics, and more specifically to appliances used in the reduction of bone fractures.

BACKGROUND

Fractures of bones, such as a fracture of a femur at one or more locations adjacent the head and neck of the femur are comparatively common. Many fracture reduction devices have been proposed for the reduction of fractures of this type. Such reduction devices basically consist of an elongate lag screw which is threaded on one end to be threadably received in the head of the femur. The lag screw is secured at the other end to a plate to form a compression hip screw assembly. The plate may include a barrel through which the screw passes. The fracture reduction device may also include bone screws for securing the plate to the femur.

The known reduction devices require that the lag screw first be inserted through an incision in a patient and into the canal of the femur. The lag screw is then advanced until the hip screw engages the head and/or neck of the femur proximal to the fracture site. The plate is then inserted through the incision and positioned over the lateral cortical wall of the shaft of the femur. At this time, the plate is assembled to the lag screw and the lag screw is tightened. When the lag screw is tightened, the head of the femur is forcibly compressed at the fracture line to the remainder of the femur. The screw may be permitted to slide in the barrel to place load on the fracture site under normal weight bearing. This sliding is known as sliding compression and promotes healing due to a phenomenon known as Wolff's law. Wolff's law teaches that load on the fracture site under normal weight bearing promotes healing and avoids atrophy of the fracture site.

Functionally, some of these devices perform quite satisfactorily for many fractures of the femur. Thus, while these devices have application and advantages relative one to another, problems and concerns remain with these devices. For example, the necessity to sequentially implant multiple components and then fit the components together results in added surgical time. As surgical time increases, costs and risks to the patient also increase.

Therefore, it would be advantageous to provide an improved hip screw assembly which is not only functional in providing the necessary stability and guidance in the reduction of the fracture, but can be efficiently, accurately and quickly implanted by the surgeon.

SUMMARY

According to one embodiment of the present disclosure, there is provided A fracture reduction assembly and method for insertion of the assembly through a surgical site in one embodiment includes a base portion including a bone contacting surface and an upper surface, a barrel with a first end portion connected to the bone contacting surface, the base portion and the barrel defining a bore extending through the barrel and the base portion and opening at the upper surface of the base portion, a screw portion including a shaft with a first diameter sized to fit within the bore and a threaded portion with a second diameter sized to not fit within the bore, wherein at least a portion of the shaft is positioned within the bore, and a retainer coupled with the shaft and having a third diameter sized to fit within a first portion of the bore but not within a second portion of the bore.

According to another embodiment of the present disclosure, a kit for a fracture reduction assembly for insertion through an incision in a patient includes at least one body including a bone contacting surface for contacting a bone and a barrel extending outwardly from the bone contacting surface of the body, at least one body defining a bore extending through the barrel and the at least one body along an axis, at least one screw portion configured to be slidingly restrained within the bore in a first direction along the axis by a threaded portion positioned outwardly of the barrel, and at least one restraining member configured to couple with the at least one screw portion to slidingly restrain the at least one screw portion within the bore in a second direction along the axis.

According to yet another embodiment of the present disclosure there is provided a method of implanting a fracture reduction assembly including making an incision in the skin of a patient, preparing a bone to receive the fracture reduction assembly, assembling the fracture reduction assembly, inserting the assembled fracture reduction assembly through the incision, embedding a screw portion of the fracture reduction assembly in a first portion of the prepared bone, and affixing a plate portion of the fracture reduction assembly to a second portion of the prepared bone.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 6 depicts a side cross sectional view of the retainer of the fracture reduction assembly of FIG. 1;

FIG. 7 depicts a side cross sectional view of the base portion of the fracture reduction assembly of FIG. 1 aligned with the screw portion of the fracture reduction assembly of FIG. 1;

FIG. 8 depicts a side cross sectional view of the screw portion of the fracture reduction assembly of FIG. 1 inserted into the barrel of the base portion of the fracture reduction assembly of FIG. 1 such that a portion of the shaft of the screw portion extends above the plate portion, and the retainer of the fracture reduction assembly of FIG. 1 aligned with the portion of the shaft;

FIG. 11 depicts a side cross sectional view of the fracture reduction assembly of FIG. 1 wherein the threaded section of the screw portion is larger than the diameter of the bore entrance and the retainer is located within an upper portion of the bore;

FIG. 12 depicts a partial side cross sectional view of the fracture reduction assembly of FIG. 1 showing the diameter of the coupled retainer to be smaller than the portion of the bore located upwardly from a protuberance at the mouth of the bore and larger than the diameter of the bore defined by the protuberance, and also showing the clearance between the retainer and the bore to be less than the extent of the retainer located within the coupling member of the shaft;

FIG. 13 depicts a fractured femur that has been prepared to receive an assembled fracture reduction assembly through an incision in accordance with principles of the invention;

FIG. 14 depicts the fractured femur of FIG. 13 after the fracture reduction assembly has been inserted through the incision and the screw portion has been embedded in the head of the femur;

FIG. 15 depicts a side plan view of the locking member of FIG. 1 that may be used to clamp the screw portion and the retainer of FIG. 1 so as to rotationally lock the screw portion with respect to the base portion while allowing axial movement of the screw portion within the barrel;

FIG. 16 depicts an end perspective view of the locking member of FIG. 15;

Corresponding reference characters indicate corresponding parts throughout the several views. Like reference characters tend to indicate like parts throughout the several views.

DETAILED DESCRIPTION

Embodiments of the present invention and the advantages thereof are best understood by referring to the following descriptions and drawings, wherein like numerals are used for like and corresponding parts of the drawings.

Figure 1:
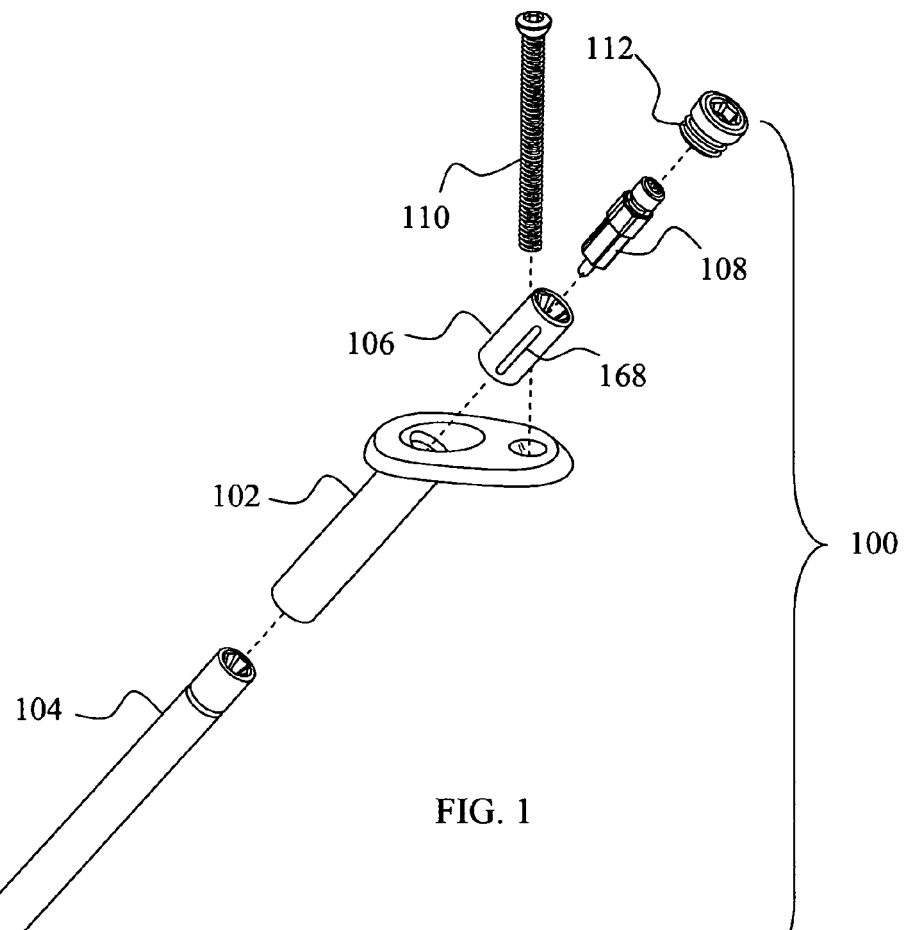
FIG. 1 depicts an exploded perspective view of a fracture reduction assembly incorporating principles of the invention.
Figure 2:
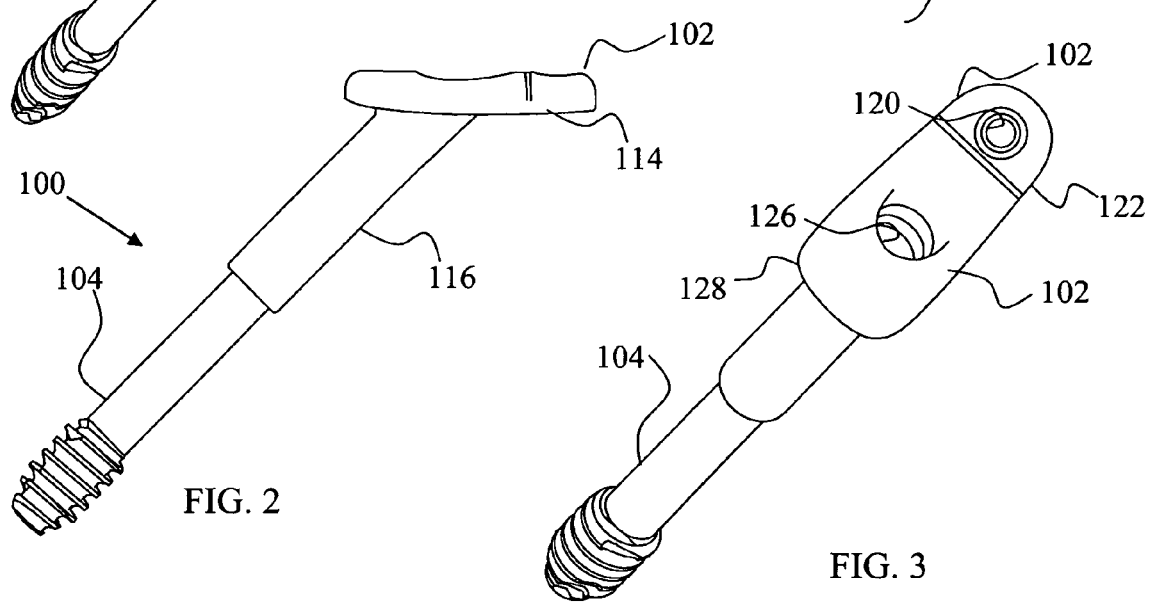
FIG. 2 depicts a side plan view of the assembled fracture reduction assembly of FIG. 1.
Figure 3:
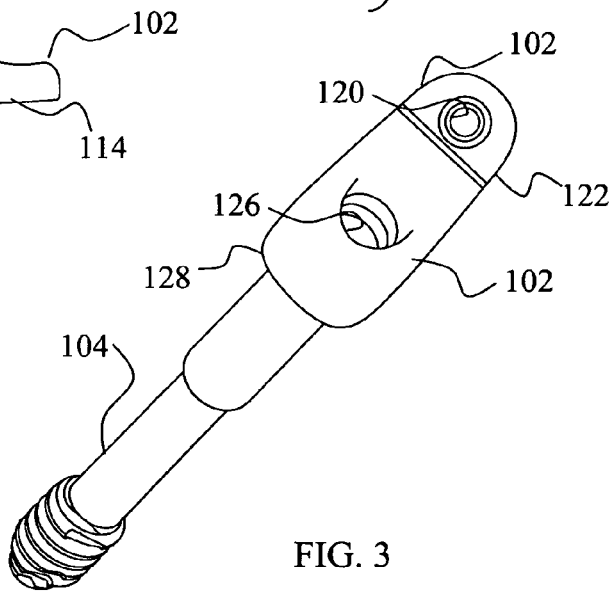
FIG. 3 depicts a top plan view of the assembled fracture reduction assembly of FIG. 1.

A fracture reduction assembly 100 is shown in FIGS. 1-3. The fracture reduction assembly 100 includes a base portion 102, a screw portion 104, a retaining sleeve 106, and a locking member 108. Screws 110 and 112 are also shown in FIG. 1. The foregoing components may be made of any suitable durable material and may be made, for example, of a titanium alloy, a stainless steel alloy, or a cobalt chromium alloy. If desired, all of the components may be made of the same material.

Figure 4:
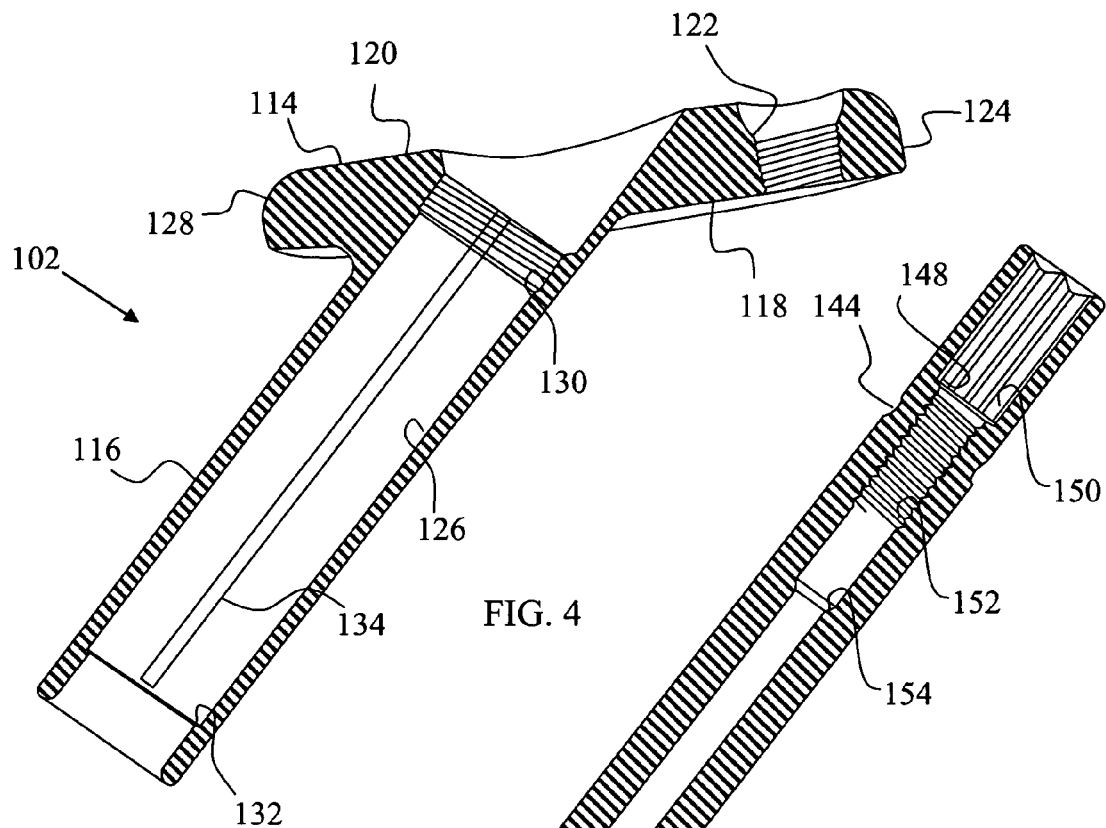
FIG. 4 depicts a side cross sectional view of the base portion of the fracture reduction assembly of FIG. 1.

The base portion 102, also shown in FIG. 4, includes a plate 114 and a barrel 116 which extends outwardly and medially from the plate 114. The plate 114 includes a bone contacting surface 118 and an outer surface 120. A threaded hole 122 is located on a distal portion 124 of the plate 114 and extends from the outer surface 120 to the bone contacting surface 118.

A bore 126 is located between the distal portion 122 and a proximal portion 128 of the plate 114. As shown in FIG. 4, the bore 126 extends from the outer surface 120 through the barrel 116. The bore 126 includes an upper threaded portion 130, a shoulder 132 and a guide slot 134. The diameter of the bore 126 is reduced at the shoulder 132 while the guide slot 134 provides a portion of the bore 126 with an increased diameter.

Figure 5:
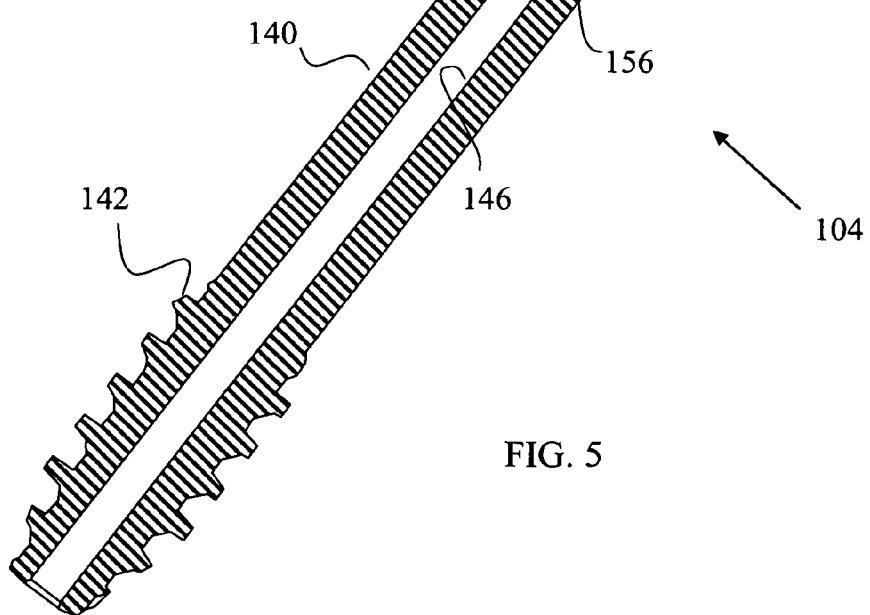
FIG. 5 depicts a side cross sectional view of the screw portion of the fracture reduction assembly of FIG. 1.

With reference to FIG. 5, the screw portion 104 includes a shaft portion 140 and a threaded portion 142. In this embodiment, the screw portion 104 is thus in the form of a lag screw incorporating cancellous threads in the threaded portion 142. A coupling member 144 is located at the upper portion of the shaft portion 140. A bore 146 extends through the shaft portion 140 and the threaded portion 142. A shoulder 148 separates an upper hexagonally shaped portion 150 of the bore 146 from a threaded portion 152. A shoulder 154 separates the threaded portion 152 of the bore 146 from a lower portion 156.

The retaining sleeve 106 which is shown in FIGS. 1 and 6 includes an upper hexagonally shaped bore 160 which is separated from a lower bore 162 by a shoulder 164. A coupling member 166 is located at the lower portion of the lower bore 162 and a guide member 168 extends along the outer surface of the retaining sleeve 106.

The assembly of the foregoing components to form the fracture reduction assembly 100 may be performed by the manufacturer and the assembly 100 packaged in a sterile container for later implantation into the patient. Alternatively, the components can be assembled in the surgery room prior to implantation. In either event, the screw portion 104 is initially aligned with the barrel 116 of the base portion 102 as shown in FIG. 7. The shaft portion 140 is sized to have a diameter that is slightly less than the diameter of the bore 126 defined by the smaller diameter of the shoulder 132. In alternative embodiments, shapes other than circular shapes may be used so long as the shaft fits within the bore. The shaft portion 140 is then moved in the direction of the arrow 170 of FIG. 7 and inserted into the bore 126.

The threads of the threaded portion 142 define a diameter that is larger than the smaller diameter of the shoulder 132. Accordingly, movement of the screw portion 104 in the direction of the arrow 170 is restricted once the threaded portion 142 is adjacent to the barrel 116. As shown in FIG. 8, however, the shaft portion 140 is sized such that the coupling member 144 is positioned outwardly of the bore 126 before the threaded portion 142 contacts the barrel 116. Next, the retaining sleeve 106 is aligned with the shaft portion 140 which extends above the outer surface 120 of the plate 114. As shown in FIG. 8, the retaining sleeve 106 is oriented such that the coupling member 166 is adjacent to the shaft portion 140.

Figure 9:
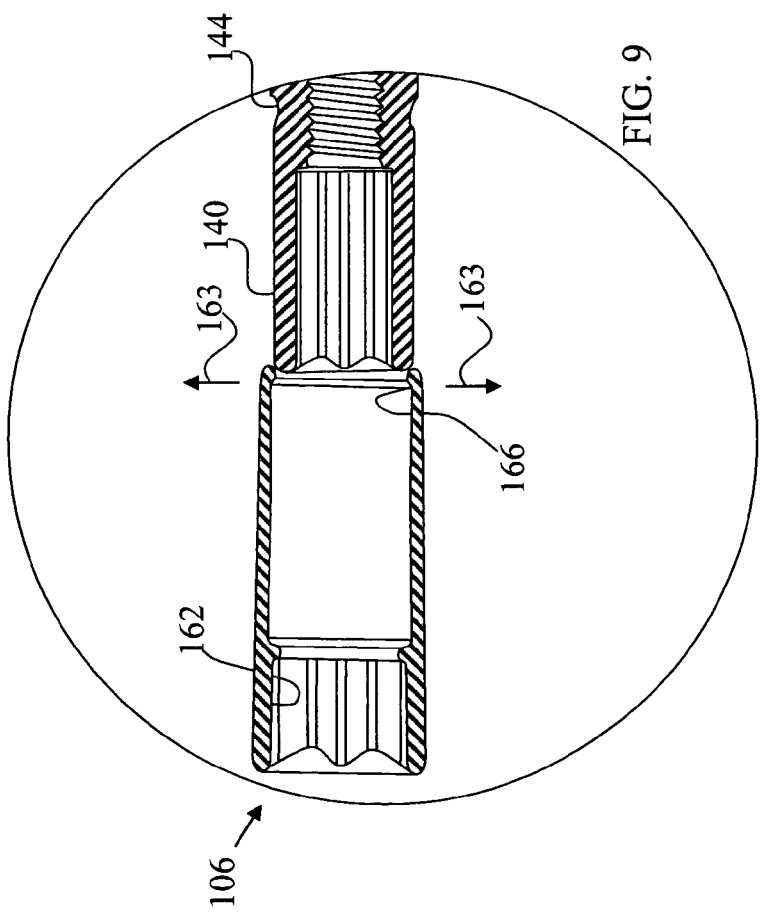
FIG. 9 depicts a partial cross sectional view of the retainer of FIG. 8 contacting the outer surface of the shaft as the shaft is inserted into the retainer, thereby causing the retainer to flex outwardly.

Next, the retaining sleeve 106 is moved in the direction of the arrow 172 (see FIG. 8) until the coupling member 166 contacts the shaft portion 140. As shown in FIG. 9, the coupling member 166 defines a diameter which is less than the diameter of the shaft portion 140. Accordingly, as additional force is applied in the direction of the arrow 172, the coupling member 166 flexes radially outward as indicated by the arrows 163 of FIG. 9, thereby allowing additional movement of the retaining sleeve 106 onto the shaft portion 140. Movement of the retaining sleeve 106 continues until the coupling member 166 is aligned with the coupling member 144 of the shaft portion 140.

Figure 10:
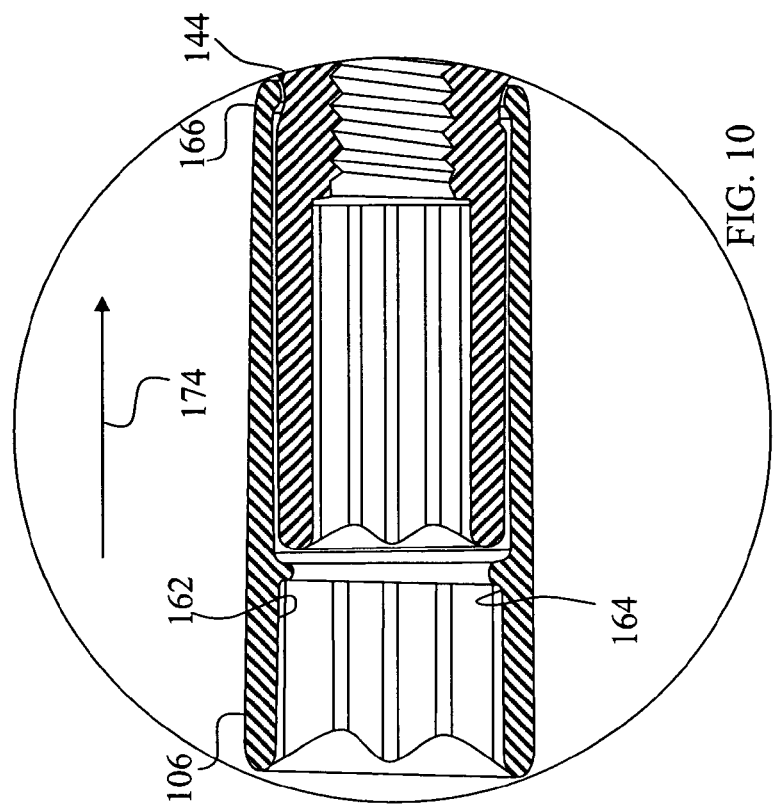
FIG. 10 depicts a partial cross sectional view of the retainer of FIG. 8 after flexing inwardly to couple with a coupling member of the shaft, and positioned above the base portion.

The reduced diameter of the shaft portion 140 at the coupling member 144 allows the coupling member 166 to flex inwardly toward the original shape of the coupling member 166 as shown in FIG. 10. The diameter of the lower bore 162, the shaft portion 140, the coupling member 144 and the coupling member 166 are selected such that a tight fit is achieved between all of the components. Additionally, when the coupling members 144 and 166 are coupled, the end portion of the shaft portion 140 is adjacent to the shoulder 164, restraining further movement of the restraining sleeve 106 onto the shaft portion 140.

Once the retaining sleeve 106 is positioned on the shaft portion 140, the screw portion 104 is slidably coupled with the base portion 102. Specifically, movement of the screw portion 104 outwardly of the base portion 102 in a direction above the outer surface 118 (to the left as viewed in FIG. 10) is restrained by the threaded portion 142 abutting the barrel 114 (see FIG. 8). Movement of the screw portion 104 in the direction of the arrow 174 from the position of FIG. 10 is allowed by aligning the guide member 168 (see FIG. 1) with the guide slot 134 (see FIG. 4). The diameter of the restraining sleeve 106 at the guide member 168 is slightly less than the diameter of the bore 126 at the guide slot 134 and the diameter of the remainder of the restraining sleeve 106 is slightly less than the diameter of the remainder of the bore 126 defined by the smaller diameter of the shoulder 132. Thus, the retaining sleeve 106 is allowed to move into the portion of the bore 126 between the threaded portion 130 and the shoulder 132 as shown in FIG. 11.

As shown in FIG. 12 the diameter of the retaining sleeve 106 is larger than the diameter of the bore 126 defined by the smaller diameter of the shoulder 132. Accordingly, movement of the screw portion 104 outwardly of the barrel 116 in a direction away from the base 102 (to the right as viewed in FIG. 12) is restrained by contact between the retaining sleeve 106 and the shoulder 132. Thus, the screw portion 104 is slidably retained within the barrel 116. The securing or retaining of the screw portion 104 in the barrel 116 provides a fracture reduction assembly 100 that may be surgically implanted as an assembly resulting in fewer steps in the surgical procedure than required for prior art lag screws which are implanted as individual components and assembled in vivo.

By way of example, FIG. 13 depicts a femur 10 with an intertrochanteric fracture 12 which separates the head 14 and neck 16 of the femur 10 from the shaft 18 of the femur 10. The fracture 12 extends from a greater trochanter 20 to a lesser trochanter 22. While the femur 10 and the intertrochanteric fracture 12 are used to describe a procedure incorporating the use of the fracture reduction assembly 100, the fracture reduction assembly 100 may also be used with other bones and with fractures having different locations.

After the fracture reduction assembly 100 has been assembled as described above, an incision 24 is made in the skin of the patient and the femur 10 is exposed in accordance with acceptable procedures. The femur 10 is then prepared to receive the fracture reduction assembly 100 by reducing the fracture 12 and drilling bores 26 and 28. The bore 26 has a diameter corresponding to the diameter of the shaft portion 140 and extends from the end portion of the bore 28 into the neck 16 and/or head 14. The bore 28 has a diameter corresponding to the diameter of the barrel 116. The bore 28 extends from the surface of the femur 10 to a depth corresponding to the length of the barrel 116.

Next, the fracture reduction assembly 100 is inserted through the incision 24 in the direction of the arrow 176. The screw portion 102 is inserted through the bore 28 and into the bore 26. The threaded portion 142 of the screw portion 102 has a diameter that is larger than at least a portion of the bore 26. Accordingly, the threaded portion 142 bites into the neck 16 and/or head 14 firmly engaging the femur 10 as shown in FIG. 14.

Once the screw portion 142 is firmly engaged with the femur 10, the base portion 102 is slid along the shaft portion 140 in the direction of the arrow 178 of FIG. 14 into contact with the femur 10. The bone contacting surface 118 of the base portion 102 is shaped for cooperation with the lateral aspect of the shaft 18. Since the shaft 18 is generally cylindrical, the bone contacting surface 118 is generally concave in the horizontal plane to conform to the shaft 18. The bone contacting surface 116 is slightly convex in the vertical plane to conform to the condylar portion of the femur 10. Thus, the base portion 102 contacts a substantial portion of the femur 10 about the bore 28 as shown in FIG. 14.

Next, the screw portion 104 is rotationally secured within the barrel 116 with the locking member 108. The locking member 108, shown in FIGS. 15 and 16, includes a housing 200 with an upper hexagonal portion 202 and a lower hexagonal portion 204. A threaded member 206 is slidingly constrained within the housing 200. The lower hexagonal portion 204 is formed complementary to the upper hexagonally shaped portion 150 of the bore 146 in the screw portion 104 and the upper hexagonal portion 202 is formed complementary to the hexagonally shaped upper bore 160 of the retaining sleeve 106.

Figure 17:
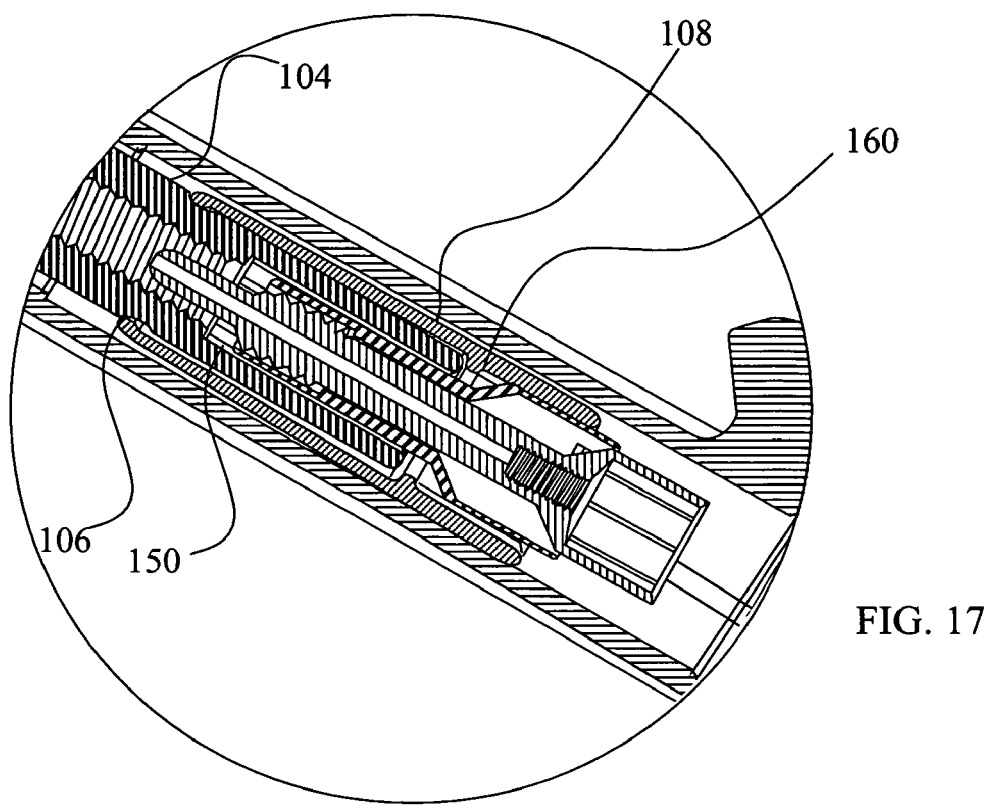
FIG. 17 depicts the locking member of FIG. 15 with one hexagonal portion inserted within the hexagonal portion of the screw portion and a second hexagonal portion inserted within a hexagonal portion of the retainer.
Figure 18:
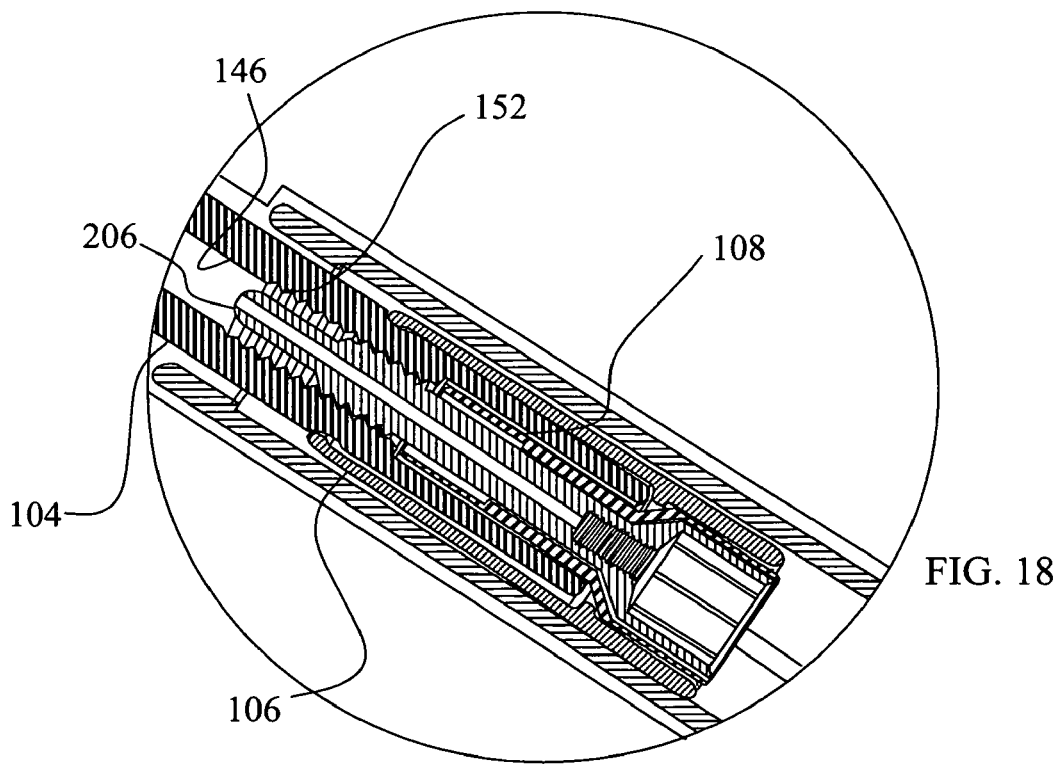
FIG. 18 depicts the locking member of FIG. 15 with one hexagonal portion inserted within the hexagonal portion of the screw portion and a second hexagonal portion inserted within a hexagonal portion of the retainer, and a threaded member threaded into the threaded portion of the screw portion.

Accordingly, the locking member 108 may be inserted into the hexagonally shaped portion 150 and the hexagonally shaped upper bore 160 as shown in FIG. 17 thereby rotationally coupling the screw portion 104 and the retaining sleeve 106. Because the retaining sleeve 106 is rotationally constrained by the coupling of the guide member 168 with the guide slot 134, the screw portion 104 is also rotationally constrained. The locking member 108 is then axially coupled with the screw portion 104 and the retaining sleeve 106 by threading the threaded member 206 into the threaded portion 152 of the bore 146 as shown in FIG. 18.

While the screw portion 104 is locked with respect to rotation, the screw portion 104 is axially movable with respect to the barrel 116. So as to ensure that the retaining sleeve 106 does not back out of the bore 146, the screw 110 is threaded with the upper threaded portion 130 of the base portion 102.

Figure 19:
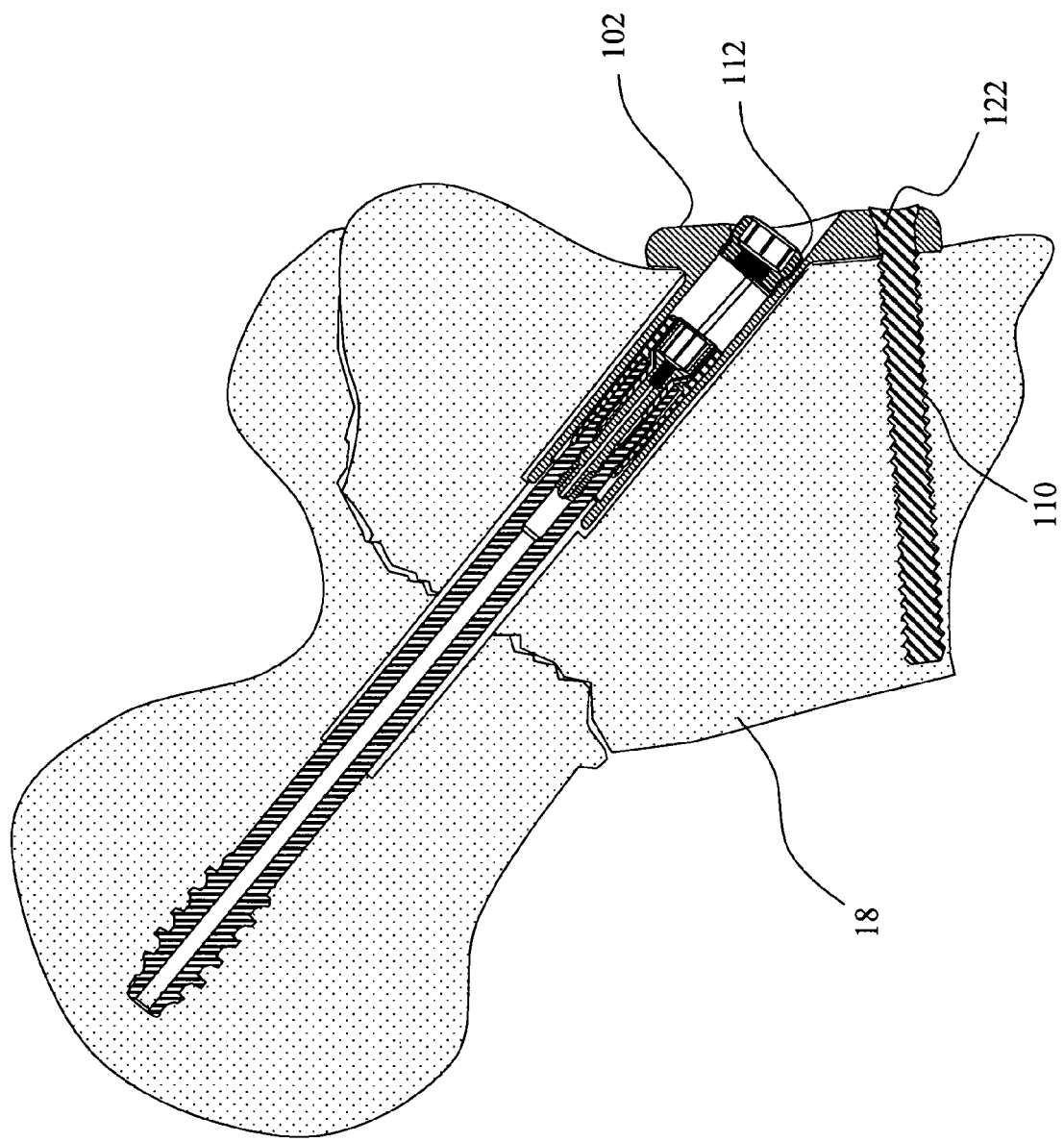
FIG. 19 depicts the fracture reduction assembly of FIG. 1 fully implanted on the femur of FIG. 14.

As shown in FIG. 19, the screw 110 may also be threaded into the threaded hole 122. In this embodiment, the screw 110 includes a threaded head configured to lock in the threaded hole 122 and secure the base portion 102 to the lateral aspect or lateral cortex wall of the shaft 18. In alternative embodiments, a non locking screw such as a cortical screw with a non threaded head may be used. A kit may include a variety of locking and non-locking screws of different lengths for use in the threaded hole 122.

FIG. 19 further shows the screw 112 engaged with the upper threaded portion 130 of the base portion 102. The screw 112 thus restricts outward movement of the clamped screw portion 104 and retaining sleeve 106 which can move axially along the barrel 116.

Figures 20, 21:
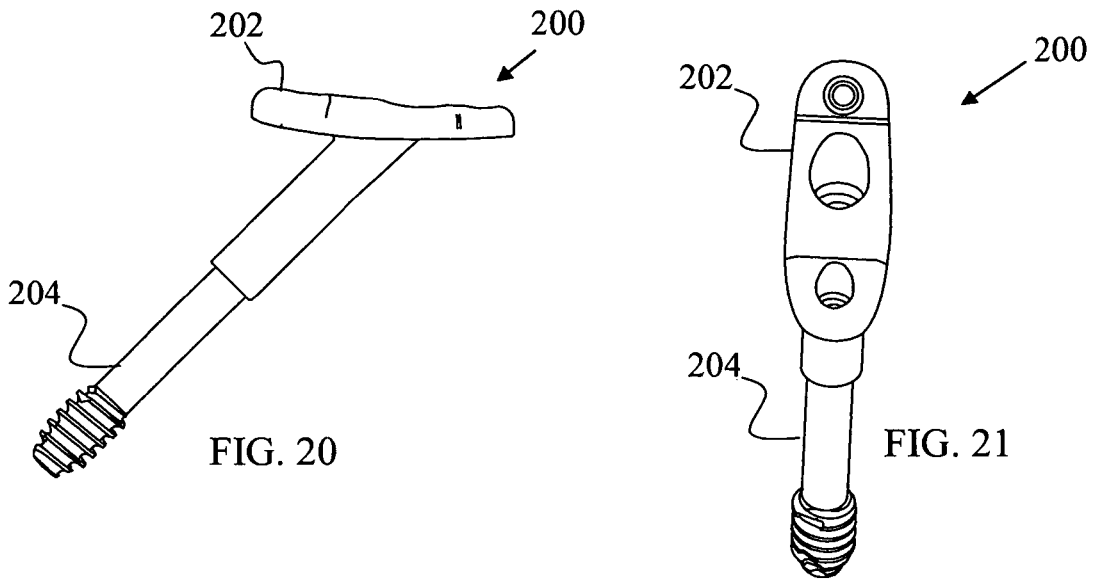
FIGS. 20 and 21 depict an alternative embodiment of a fracture reduction assembly incorporating a base with an extended proximal portion providing a second hole for receiving a second bone fastener.
Figures 22, 23:
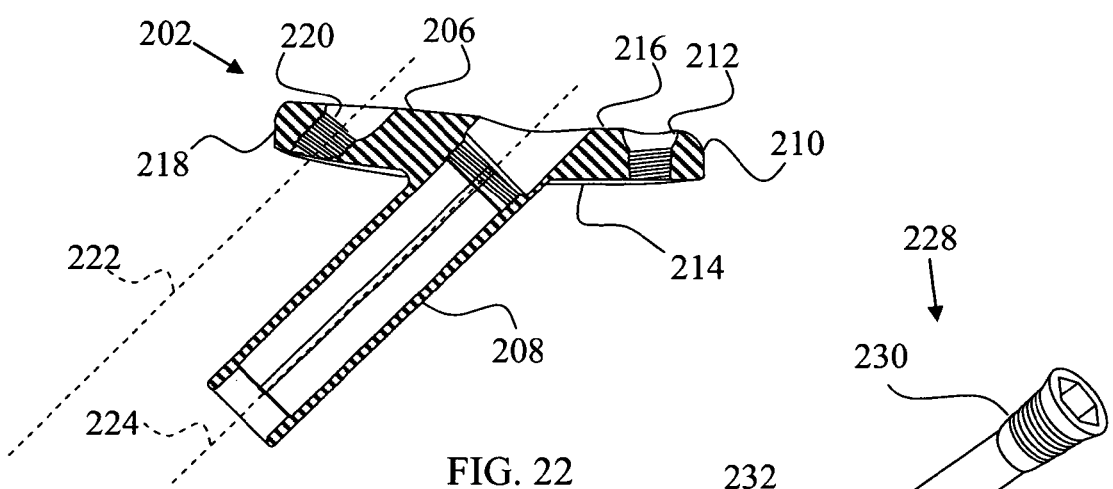
FIG. 22 depicts a side cross sectional view of the base portion of the fracture reduction assembly of FIGS. 20 and 21.
FIG. 23 depicts a side perspective view of a bone fastener that may be inserted through the second hole of the fracture reduction assembly of FIGS. 20 and 21.

FIGS. 20-21 depict a fracture reduction assembly 200. The fracture reduction assembly 200 is substantially similar to the fracture reduction assembly 100 and includes a base 202 and a screw portion 204. In one embodiment, the only difference between the fracture reduction assembly 200 and the fracture reduction assembly 100 is the configuration of the base 202. With further reference to FIG. 22, the base portion 202 includes a plate 206 and a barrel 208. A distal portion 210 of the plate 206 includes a threaded hole 212. The plate 206 further includes a bone contacting surface 214 and an outer surface 216. The barrel 208 and the distal portion 210 are similar to components discussed with reference to the fracture reduction assembly 100 and are not further described herein.

A proximal portion 218 of the plate 206, however, is configured to provide additional support to the lateral aspect of the greater trochanter. To this end, proximal portion 218 extends farther from the barrel 208 than the proximal portion 128 extends from the barrel 116 of the fracture reduction assembly 100. This allows for an additional threaded hole 220 to be positioned proximally from the barrel 208. In the embodiment of FIG. 22, the threaded hole 220 is oriented to define an axis 222 that is substantially parallel to the axis 224 defined by the barrel 208. In alternative embodiments, the additional hole may be unthreaded.

An anti-rotation screw 228 shown in FIG. 23 may be used with the threaded hole 220. The anti-rotation screw 228 includes tapered external threads formed on a head 230. The threaded head 230 mates with tapered internal threads in the threaded hole 220 to lock the anti-rotation screw 228 to the plate 202. The anti-rotation screw 228 further includes a shaft 232 and cancellous external threads 234 which engage cancellous bone in the head 44 of the femur 40. In one embodiment, the screw 228 is a 6½ millimeter screw although screws of different sizes and lengths may be used.

Figure 24:
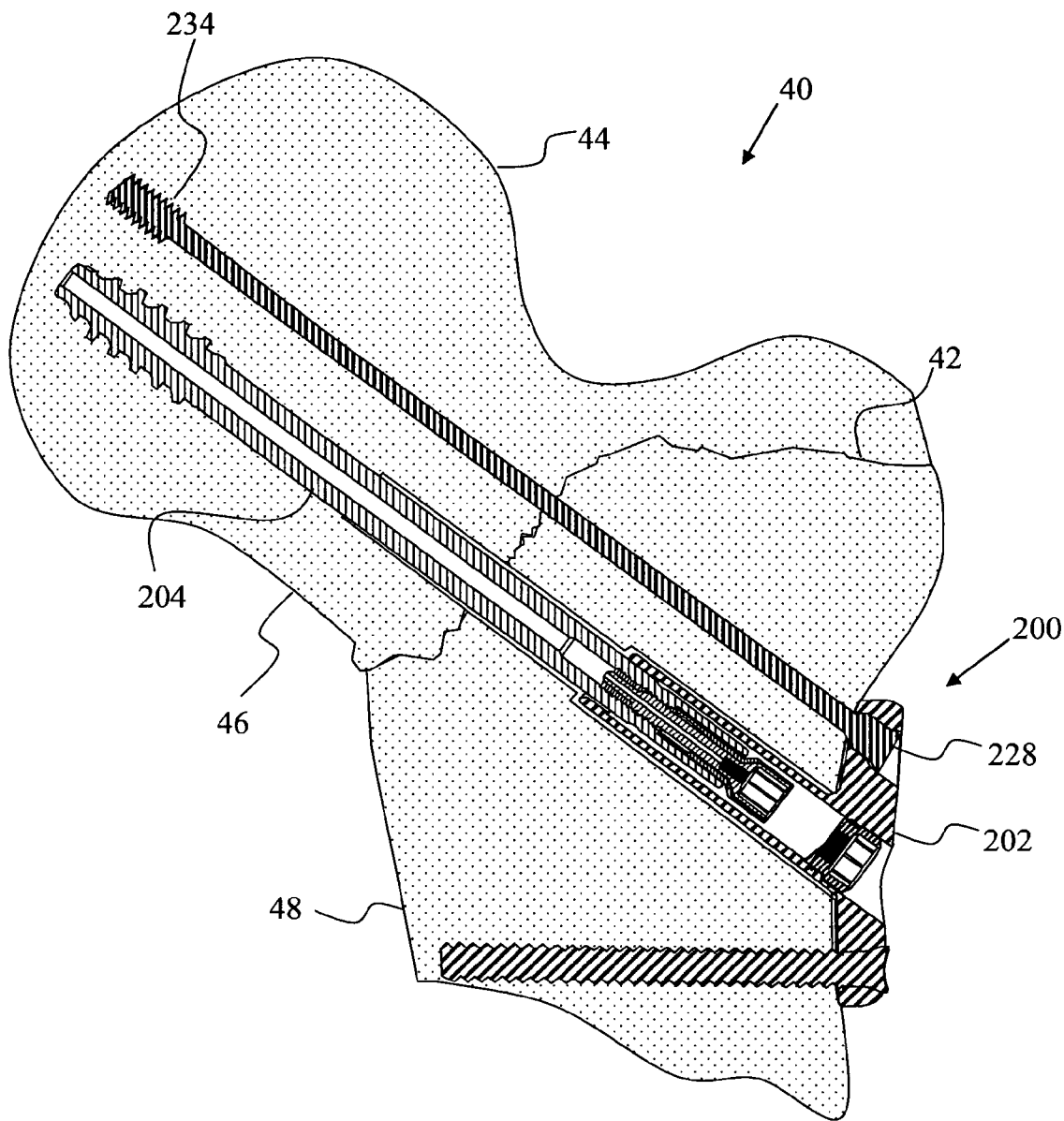
FIG. 24 depicts the fracture reduction assembly of FIGS. 20 and 21 attached to a fractured femur with the threaded portion of the screw portion embedded in the head of the femur along with the threaded portion of the bone fastener of FIG. 23.

The orientation of the axes 222 and 224 allow a long screw such as the screw 228 to provide additional fixation with the neck and or head of a femur without contacting the screw portion 204. By way of example, in FIG. 24, the fracture reduction assembly 200 is depicted mounted to a femur 40. The femur 40 includes a fracture 42 separating the head 44 and the neck 46 from the shaft 48. Both the screw portion 204 and the screw 228 extend across the fracture 42, thereby providing additional fixation between the fracture reduction system 200 and the femur 40. While the screw 228 is shown to have substantially the same length as the screw portion 204, in alternative embodiments shorter screws or screws with non-threaded heads may be used.

Although the present invention has been described with respect to certain preferred embodiments, it will be appreciated by those of skill in the art that other implementations and adaptations are possible. Moreover, there are advantages to individual advancements described herein that may be obtained without incorporating other aspects described above. Therefore, the spirit and scope of the appended claims should not be limited to the description of the preferred embodiments contained herein.

We claim:

1. A fracture reduction assembly for fixation of a fractured bone, comprising: a base portion including a bone contacting surface for contacting a bone and an upper surface opposite to the bone contacting surface;
   a barrel with a first end portion connected to the bone contacting surface, the base portion and the barrel defining a bore extending through the barrel and the base portion and opening at the upper surface of the base portion;
   a screw portion including a shaft with a first diameter sized to fit within the bore and a threaded portion with a second diameter sized to not fit within the bore, wherein at least a portion of the shaft is positioned within the bore; and
   a retainer coupled with the shaft and having a third diameter sized to fit within a first portion of the bore but not within a second portion of the bore; wherein the shaft further comprises a coupling member; the retainer is coupled with the coupling member of the shaft; the length of the screw portion between the coupling member and the threaded portion with a second diameter sized to not fit within the bore is greater than the length of the bore from the at least one diameter to the upper surface of the base; the coupling member of the shaft comprises a recessed area in the outer surface of the shaft; and the retainer defines a protuberance configured to fit at least partially within the recessed area.

2. The assembly of claim 1, further comprising:
   a protuberance defining a reduced diameter of the bore, wherein the reduced diameter is smaller than the second diameter and the reduced diameter is smaller than the third diameter.

3. The assembly of claim 2, wherein the protuberance is located at a second end portion of the barrel.

4. The assembly of claim 1, wherein the portion of the protuberance received within the recessed area defines a first length along an axis extending radially from the bore through the barrel, the first length greater than the clearance between the retainer and the first portion of the bore along the axis.

5. The assembly of claim 1, the base portion further defining a hole for receiving a bone fastener, the hole having an axis substantially parallel to the axis of the bore.

6. The assembly of claim 5 wherein the hole is threaded.

* * * * *

UNITED STATES PATENT AND TRADEMARK OFFICE
CERTIFICATE OF CORRECTION

| | |
|---|---|
| PATENT NO. | : 8,182,484 B2 |
| APPLICATION NO. | : 12/148617 |
| DATED | : May 22, 2012 |
| INVENTOR(S) | : Stuart R. Grant et al. |

It is certified that error appears in the above-identified patent and that said Letters Patent is hereby corrected as shown below:

<u>Column 1,</u>
Line 56, replace "provided A" with --provided a--

<u>Column 1,</u>
Line 58, after "embodiment" insert --that--

<u>Column 8,</u>
Line 49, after "claim 5" insert --,--

Signed and Sealed this
Nineteenth Day of February, 2013

Teresa Stanek Rea
*Acting Director of the United States Patent and Trademark Office*